(12) United States Patent
Holick

(10) Patent No.: US 7,906,480 B2
(45) Date of Patent: Mar. 15, 2011

(54) USE OF A PARATHYROID HORMONE PEPTIDE ANALOGS FOR THE TREATMENT OF VAGINAL ATROPHY

(76) Inventor: Michael Holick, Sudbury, MA (US)

( * ) Notice: Subject to any disclaimer, the term of this patent is extended or adjusted under 35 U.S.C. 154(b) by 1103 days.

(21) Appl. No.: 10/515,551

(22) PCT Filed: May 23, 2003

(86) PCT No.: PCT/US03/16478
§ 371 (c)(1),
(2), (4) Date: Mar. 7, 2006

(87) PCT Pub. No.: WO03/099849
PCT Pub. Date: Dec. 4, 2003

(65) Prior Publication Data
US 2006/0211608 A1 Sep. 21, 2006

Related U.S. Application Data

(60) Provisional application No. 60/382,905, filed on May 23, 2002.

(51) Int. Cl.
*A61K 38/29* (2006.01)

(52) U.S. Cl. ............................................. 514/6; 514/12

(58) Field of Classification Search ........................ None
See application file for complete search history.

(56) References Cited

U.S. PATENT DOCUMENTS

| | | |
|---|---|---|
| 4,086,196 A | 4/1978 | Tregear |
| 4,423,037 A | 12/1983 | Rosenblatt et al. |
| 4,771,124 A | 9/1988 | Rosenblatt et al. |
| 4,833,125 A | 5/1989 | Neer et al. |
| 4,968,669 A | 11/1990 | Rosenblatt et al. |
| 5,001,223 A | 3/1991 | Rosenblatt et al. |
| 5,087,562 A | 2/1992 | Rosenblatt et al. |
| 5,093,233 A | 3/1992 | Rosenblatt et al. |
| 5,116,952 A | 5/1992 | Martin et al. |
| 5,149,779 A | 9/1992 | Chorev et al. |
| 5,171,670 A | 12/1992 | Kronenberg et al. |
| 5,229,489 A | 7/1993 | Kanmera et al. |
| 5,260,065 A | 11/1993 | Mathur et al. |
| 5,317,010 A | 5/1994 | Pang et al. |
| 5,382,658 A | 1/1995 | Kronis et al. |
| 5,393,869 A | 2/1995 | Nakagawa et al. |
| 5,434,246 A | 7/1995 | Fukuda et al. |
| 5,461,064 A | 10/1995 | Cullinan |
| 5,527,772 A * | 6/1996 | Holick ............................. 514/12 |
| 5,589,452 A | 12/1996 | Krstenansky et al. |
| 5,807,823 A | 9/1998 | Krstenansky et al. |
| 5,821,255 A | 10/1998 | Roger et al. |
| 5,840,690 A | 11/1998 | Holick |
| 5,977,070 A | 11/1999 | Piazza et al. |
| 6,025,467 A | 2/2000 | Fukuda et al. |
| 6,060,077 A | 5/2000 | Meignant |
| 6,066,618 A | 5/2000 | Holick |
| 6,190,691 B1 | 2/2001 | Mak |
| 6,190,693 B1 | 2/2001 | Kafrissen et al. |
| 6,306,914 B1 | 10/2001 | de Ziegler et al. |
| 6,355,670 B1 | 3/2002 | Maclean et al. |
| 6,362,163 B1 | 3/2002 | Gardella et al. |
| 2004/0013719 A1 | 1/2004 | Holick |

FOREIGN PATENT DOCUMENTS

| | | |
|---|---|---|
| EP | 0 477 885 A2 | 4/1992 |
| WO | WO 94/02510 A2 | 2/1994 |
| WO | WO 00/23594 A1 | 4/2000 |
| WO | WO 00/31137 A1 | 6/2000 |
| WO | WO 02/28420 | 4/2002 |

OTHER PUBLICATIONS

Andersson et al., "Intrauterine release of levonorgestrel—A new way of adding progestogen in hormone replacement therapy," *Obstetrics and Gynecology* 79(6):963-967 (1992).

Clemens et al., "Parathyroid hormone-related protein and its receptors: nuclear functions and roles in the renal and cardiovascular systems, the placental trophoblasts and the pancreatic islets," *British Journal of Pharmacology* 134(6):1113-1136 (2001).

Doppelt et al., "Inhibition of the in vivo parathyroid hormone-mediated calcemic response in rats by a synthetic hormone antagonist," *Proceedings of the National Academy of Science* USA 83:7557-7560 (1986).

Goldring et al., "Response to Hormones of Cells Cultured from Human Giant Cell Tumors of Bone," *Journal of Clinical Endocrinology and Metabolism* 46(3):425-433 (1978).

Holick et al., "A parathyroid hormone antagonist stimulates epidermal proliferation and hair growth in mice," *Proceedings of the National Academy of Science* 91:8014-8016 (1994).

Keutmann et al., "Rat parathyroid hormone-(1-34) fragment: renal adenylate cyclase activity and receptor binding properties in vitro," *Endocrinology* 117(3):1230-1234 (1985).

Massfelder et al., "Parathyroid hormone-regulated peptide—a smooth muscle tone and proliferation regulatory protein," *Current Opinion in Nephrology and Hypertension* 7(1):27-32 (1998).

Nissenson et al., "Endogenous biologically active human parathyroid hormone: measurement by a guanyl nucleotide-amplified renal adenylate cyclase assay," *Journal of Clinical Endocrinology and Metabolism* 52(5):840-846 (1981).

Nussbaum et al., "Design of Analogues of Parathyroid Hormone: A Conformational Approach," *Journal of Protein Chemistry* 4(6):391-406 (1985).

Nutt et al., "Removal of partial agonism from parathyroid hormone (PTH)-related protein-(7-34)NH$_2$ by substitution of PTH amino acids at positions 10 and 11," *Endocrinology* 127:491-493 (1990).

Orloff et al., "Further evidence for a novel receptor for amino-terminal parathyroid hormone-related protein on keratinocytes and squamous carcinoma cell lines," *Endocrinology* 186(7):3016-3023 (1995).

Philbrick et al., "Defining the roles of parathyroid hormone-related protein in normal physiology," *Physiological Reviews* 76(1):127-173 (1996).

(Continued)

*Primary Examiner* — Christopher R. Tate
*Assistant Examiner* — Roy Teller
(74) *Attorney, Agent, or Firm* — Clark & Elbing LLP

(57) ABSTRACT

The invention features methods for the treatment of vaginal atrophy by administering a parathyroid hormone peptide or peptide analog and formulations thereof.

12 Claims, 1 Drawing Sheet

OTHER PUBLICATIONS

Stumpf, "Pharmacokinetics of estrogen," *Obstetrics and Gynecology* 75:(4 Suppl):9S-14S (1990).

International Search Report for PCT/US2003/16478, mailed Aug. 24, 2004.

International Preliminary Examination Report for PCT/US2003/16478, completed Sep. 10, 2004.

Supplementary European Search Report for EP 03734177, completed Sep. 24, 2009.

* cited by examiner

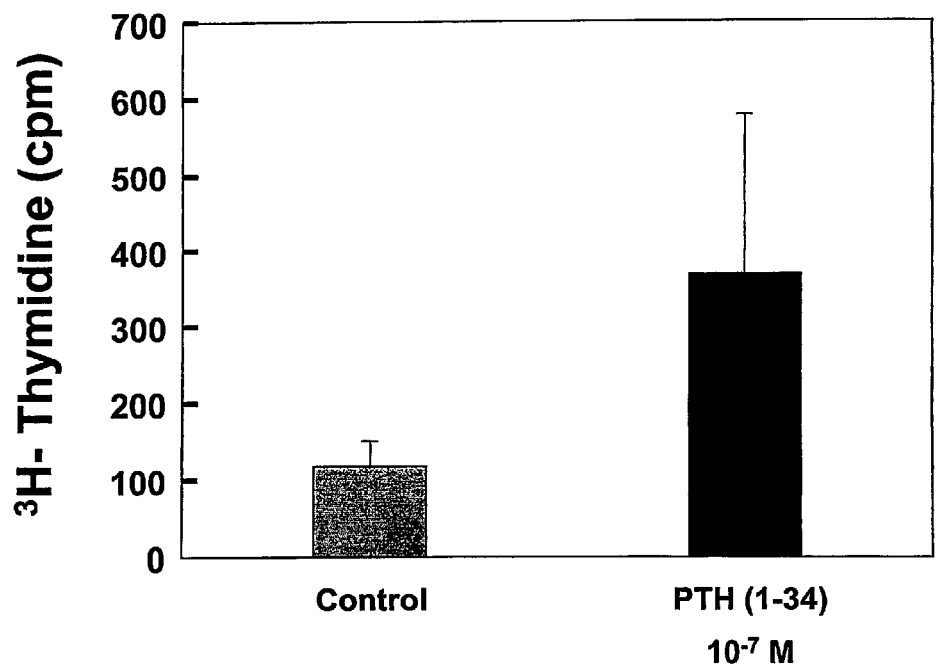

USE OF A PARATHYROID HORMONE PEPTIDE ANALOGS FOR THE TREATMENT OF VAGINAL ATROPHY

CROSS-REFERENCE TO RELATED APPLICATIONS

This application is the National Stage of International Application No. PCT/US2003/016478, filed May 23, 2003, which was published in English under PCT Article 21(2). This application also claims benefit of U.S. Provisional Application No. 60/382,905, filed May 23, 2002.

BACKGROUND OF THE INVENTION

This invention relates to methods for inhibiting or treating vaginal atrophy.

Vaginal atrophy is a condition occurring in 75 to 85% of postmenopausal women. Vaginal atrophy is marked by a significant thinning of the mucosa of the vagina. Symptoms resulting from the abnormally thin vaginal mucosa include vaginal dryness, discomfort, itching, dyspareunia, infection, inflammation, ulcers, discharge, and bleeding. Urinary incontinence and urinary tract infections can also accompany vaginal atrophy.

The normal vaginal mucosa consists of a stratified squamous epithelium, which undergoes multiple changes throughout the life of a woman. During puberty, the vaginal epithelium is highly proliferative, thick, and contains abundant glycogen. After menopause, estrogen levels decrease resulting in a decreased glycogen content and general reduction in vaginal secretions. In post-menopausal women suffering from vaginal atrophy, the vaginal mucosa thins and the cellular make-up changes significantly. The thin vaginal mucosa characteristic of vaginal atrophy lacks maturation, i.e., it consists of numerous parabasal cells and little or no superficial and intermediate cells, resulting in further decreased glycogen deposits and a higher pH. This loss of lubrication and increased pH can lead to many of the symptoms associated with vaginal atrophy, e.g., increased susceptibility to infections, vaginal dryness, and dyspareunia.

Vaginal atrophy is caused primarily by an estrogen deficiency; the mucosa of the vagina is an estrogen sensitive tissue and a well-known target organ for estrogen. At the time of menopause, the levels of estrogen produced by the ovaries rapidly decrease. This decrease in estrogen has pronounced effects on the vagina causing a rapid acceleration in the natural process of atrophy. Estrogen replacement therapy is often beneficial in treating vaginal atrophy. The administration of exogenous estrogen can dramatically reverse the atrophic process by causing the vaginal epithelium to undergo proliferation and maturation, resulting in an increase in vaginal mucosal thickness. The administration of exogenous estrogen also influences glycogen deposits and vaginal acidity, which can reduce susceptibility to bacterial infections.

Many postmenopausal women are however unable to use estrogens due to medical contraindications such as a history of breast, endometrial, ovarian or cervical cancer and various hematological disorders. In addition, some postmenopausal women who would benefit from estrogen replacement do not receive replacement due to fears of estrogens in general or undesirable side effects such as nausea, breast tenderness, vaginal bleeding, and fluid retention. The treatment of vaginal atrophy in patients who do not use exogenous estrogen is a significant therapeutic problem; most of these women are forced to endure their symptoms due to the lack of effective treatment alternatives. Clearly, an effective and safe agent, which positively affects the underlying physiology and thus improves the qualitative aspects of vaginal properties in post-menopausal women, would be useful.

Parathyroid hormone (PTH) is an important regulator of calcium and phosphorus concentration in extracellular fluids. PTH is synthesized as a preprohormone and, after intracellular processing, is secreted as an 84 amino acid polypeptide. PTH release and synthesis are controlled principally by the serum calcium level; a low level stimulates and a high level suppresses both hormone synthesis and release. PTH, in turn, maintains the serum calcium level by indirectly or directly promoting calcium entry into the blood at three sites of calcium exchange; gut, bone, and kidney. PTH acts directly to raise extracellular calcium by its actions on bone and kidney and indirectly by increasing the production of $1,25(OH)_2D3$ to enhance intestinal calcium absorption. A variety of cells, including kidney cells, lymphocytes, and osteosarcoma cells, possess receptors for PTH. A variety of in vitro and in vivo tests have been developed to assay for PTH activity. These include the measurement of cyclic AMP production in isolated canine kidney membranes, osteosarcoma cells, and human fibroblasts. In addition, a multiresponse PTH assay has been developed to measure both agonist and antagonist properties of PTH analogs.

Cultured human keratinocytes also make a PTH related protein, known as PTHrP. PTHrP was isolated from a human lung cancer cell line, and full-length complementary DNA clones encoding it have been inserted into expression vectors used to produce the peptide in mammalian cells. The clones were found to encode a family of distinct peptide hormones, one of which is a peptide of 36 amino acids that has significant homology with PTH in the amino terminal region; of the first 16 residues of this protein, eight were found to be identical to human PTH. In addition to regulating extracellular calcium levels, PTHrP is also a potent regulator of cellular proliferation, differentiation, and death of many cell types.

The similar activity profiles of PTH and PTHrP can be explained by their interaction with a common receptor, the type I PTH/PTHrP receptor, which is expressed abundantly in bone and kidney. In both hPTH and hPTHrP, the region encompassing amino acids 15-34 contains the principal determinants for binding to the PTHPTHrP receptor. (The format xPTH (y-z) is used hereafter to identify the peptide, where x refers to the species (e.g. h for human and b for bovine), y refers to the starting amino acid in the PTH amino acid sequence and z refers to the ending amino acid.) Although these regions show only minimal sequence homology (only three amino acid identities), both hPTH(15-34) (SEQ ID NO: 7) and hPTHrP(15-34) (SEQ ID NO: 22) peptides can block the binding of either hPTH(1-34) or hPTHrP (1-34) (SEQ ID NOs: 5, 17) to the PTHPTHrP receptor. A type II PTH receptor was also identified in lymphocytes and keratinocytes, as well as in insulinoma and squamous carcinoma cells (Orloffet al., *Endocrinology* 186:3016-3028, 1995). Another additional receptor, the PTH-2 receptor, was also recently identified and shown to respond predominantly to PTH but not to PTHrP.

Structure function analysis of PTHPTHrP has facilitated the design of many peptides, which can function as either PTHPTHrPPTH-2 receptor agonists or PTHPTHrPPTH-2 receptor antagonists. Many of these peptides are described in the literature. For example, some of the known peptide agonists include bPTH (1-34), hPTH(1-34), [Nle$^{8,18}$, Tyr$^{34}$] bPTH (3-34)NH$_2$, hPTHrP (1-34), hPTHrP (1-36), (SEQ.ID-.NOs:4, 5, 13, 17, 18; see for reference Nussbaum et al., *J. Prot. Chem.* 4:391-406, 1985; Keutman et al., *Endocrinology* 117:1230-1234, 1985, Orloff et al., *Endocrinology* 186:3016-

3028, 1995). Peptides which are known to have antagonistic functions include hPTH(7-34), [Nle$^{8,18}$, Tyr$^{34}$]bPTH (7-34) NH$_2$, [Tyr$^{34}$]bPTH (7-34)N$_2$, hPTHrP(7-34), [Leu$^{11}$,D-Trp$^{12}$]hPTHrP(7-34)NH$_2$, [Asn$^{10}$Leu$^{11}$]hPTHrP(7-34)NH$_2$, and [Asn$^{10}$,Leu$^{11}$,D-Trp$^{12}$]hPTHrP(7-34)NH$_2$(SEQ.ID-.NOs: 8, 14, 15, 19, 24-26; see for reference Nutt et al. *Endocrinology* 127:491-493, 1990; Doppelt et al., *Proc. Natl. Acad. Sci. USA* 83:7557-7560, 1986; and U.S. Pat. Nos. 6,362,163 and 5,527,772). These peptide agonists and antagonists have been used previously to induce or to block various PTHPTHrPPTH-2 receptor functions including proliferation, differentiation, and stimulation of cyclic AMP (cAMP) production.

SUMMARY OF THE INVENTION

The present invention brings together two seemingly divergent areas of research: therapeutic treatments for vaginal atrophy and the use of PTH peptide analogs to regulate cellular proliferation. The present invention is based on the discovery that PTH peptides, such as of hPTH(1-34), hPTHrP (1-34) (SEQ ID NOs: 5, 17), and their analogues, can enhance vaginal epithelial cell growth in patients suffering from vaginal atrophy.

At the most general level, the invention provides for the therapeutic use of hPTH(1-34), hPTHrP(1-34), or a PTH analog for the treatment of vaginal atrophy.

Accordingly, in a first aspect, the invention features a method for the treatment of vaginal atrophy. The method includes the steps of administering to a patient the peptide hPTH(1-34), hPTHrP(1-34), hPTH(7-34), hPTHrP(7-34), or a PTH analog in a dosage sufficient to enhance vaginal epithelial cell growth. As used herein "PTH analog" includes any peptide that is at least five amino acids long, and has at least 10% (more preferably 50% or greater, and most preferably 75%, or greater) sequence identity with a sequence within the 34 amino acid N-terminal region of hPTH or hPTHrP, and is capable of inducing DNA synthesis or vaginal cell growth in vitro. Vaginal cell growth is induced when there is an increase of at least 20% in the total number of cells.

Peptides can also be chosen based on their ability to induce DNA synthesis or enhance skin cell or vaginal cell growth in vivo. As used herein, an induction of DNA synthesis is considered an increase of at least 20% in the rate of DNA synthesis after treatment as compared to untreated cells. As used herein, enhancement of slin cell or vaginal cell growth in vivo refers to a 10% or greater (more preferably 20% or greater, and most preferably 50% or greater) increase in the total number of cells after treatment as compared to untreated cells.

Some examples of peptides which are used in the present invention are: hPTH(7-31), hPTH(5-34), bPTHrP(5-36), [Nle$^{8,18}$, Tyr$^{34}$]bPTH (7-34)NH$_2$, [Tyr$^{34}$]bPTH (7-34)NH$_2$, hPTHrP(7-31), hPTHrP(5-36), or hPTHrP(5-34) (SEQ ID NOs.: 8-10, 14, 15, 19-21). These peptides have been previously shown to block the inhibition of proliferation or stimulation of differentiation in vitro of cultured human keratinocytes by hPTH(1-34), hPTHrP(1-34), or 1,25(OH)$_2$D3 (see U.S. Pat. Nos. 5,527,772, 5,840,690 and 6,066,618).

In the present invention, the peptide can also include any peptide which is at least eight amino acids long or which contains between 25 and 42 amino acids and has at least 75% sequence identity with the 34 amino acid N-terminal region of hPTH or hPTHrP and is capable of inducing DNA synthesis or vaginal cell growth in vitro.

The peptide can be modified in any of a variety of standard chemical ways, e.g., the carboxy-terminal amino acid can be made into a terminal amide group; the amino-terminal residue can be modified with groups to, e.g., enhance lipophilicity; the peptide can be chemically glycosylated to increase stability or in vivo half-life; and D-amino acids can be substituted for L-isomers in the peptide.

In another related aspect, the invention features a method of treating vaginal atrophy in a human patient comprising administering to the patient a peptide that is a PTH/PTHrP receptor antagonist or PTH-2 receptor antagonist. For example, a known peptide antagonist for the PTH-2 receptor consists of the amino acid sequence of hPTHrP with alterations at residue 23 (SEQ ID NO: 18). A single amino acid substitution of tryptophan for phenylalanine at position 23 of hPTHrP, [Trp$^{23}$]PTHrP(1-36) (SEQ ID NO: 23) is a particularly potent antagonist for the PTH-2 receptor.

Several peptide antagonists for the PTH/PTHrP receptor have been identified which are useful for this invention. Such peptides include any peptide having the amino acid sequence of hPTHrP with alterations at residues 10, 11 or 12. Examples of such alterations include: [Leu$^{11}$,D-Trp$^{12}$]hPTHrP (7-34) NH$_2$, [Asn$^{10}$Leu$^{11}$]hPTHrP(7-34)NH$_2$, and [Asn$^{10}$,Leu$^{11}$,D-Trp$^{12}$]hPTHrP (7-34)NH$_2$ (SEQ ID NOs: 24-26).

The peptide can be provided to a patient suffering from vaginal atrophy vulvovaginally, intravaginally, intracervically, subcutaneously, or orally. If desired, the peptide is combined with a pharmaceutically acceptable carrier substance. When necessary, zinc oxide is topically administered to the vulvovaginal area prior to the administration of the peptide to a patient suffering from vaginal atrophy.

The method of treating vaginal atrophy described in the present application can also include administering to the patient a PTH peptide analog that is encapsulated within a liposome, which comprises at least two distinct lipids, a primary lipid and a secondary lipid, the primary lipid constituting the greatest proportion, by weight, of any single lipid material forming the bilayers of said vesicle, the primary lipid being selected from the group consisting of $C_{12}$-$C_{18}$ fatty alcohols, $C_{12}$-$C_{18}$ glycol monoesters, $C_{12}$-$C_{18}$ glyceryl mono- and diesters, and mixtures thereof, and the primary lipid further having the property that it will form a lipid vesicle in the absence of the secondary lipid, and the secondary lipid being present in an amount sufficient to allow formation of the lipid vesicles, the secondary lipid being selected from the group consisting of quaternary dimethyldiacyl amines, polyoxyethylene acyl alcohols, polyglycerols, sorbitan fatty acid esters, fatty acids and their salts, and mixtures thereof.

The method of treating vaginal atrophy described herein also include administering to the patient a PTH peptide analog to the cervical and/or vaginal mucosa of a patient by means of a solution, gel, suspension, cream, ointment, foam, pessary, or tablet containing the PTH peptide analog.

Any of the forgoing formulations can further include a zinc salt. Suitable zinc salts include water-soluble organic salts having relatively low molecular weights (including zinc acetate, butyrate, gluconate, glycerate, glycolate, lactate, propionate, ascorbate, citrate, aspartate, picolinate, orotate, etc., or combinations thereof). Highly ionizing zinc salts, such as chloride, bromide, oxide, bisulfate, sulfate, bicarbonate, carbonate, nitrate, or combinations thereof, can also be used.

This invention also features a kit that includes: (i) the peptide hPTH(1-34), hPTHrP(1-34), hPTH(7-34), hPTHrP (7-34), or a PTH analog that is capable of inducing DNA synthesis or vaginal cell growth in vitro., in a dosage sufficient to enhance vaginal epithelial cell growth, and (ii) an applicator.

By "antagonist" is meant any peptide capable of inhibiting receptor activity. Inhibition of receptor activity can be determined using art-known ligand/receptor cellular response or binding assays such as those described in U.S. Pat. No. 6,362,163. For example, radio/receptor binding assays such as those described in Orloff et al. (*Endocrinology* 186:3016-3028, 1995) can be used to measure receptor binding and intracellular cAMP levels can be measured to assess receptor activity. Antagonistic function can also be measured by the ability to reduce the inhibition of proliferation or stimulation of differentiation in vitro of cultured human keratinocytes by hPTH (1-34), hPTHrP(1-34), or 1,25(OH)$_2$D3, also described below.

By "differentiation" is meant the specialization of a cell or the acquisition of specific characteristics or functions that distinguish it from the original cell. As used herein, differentiation refers to a cell that is no longer actively undergoing cell division or mitosis.

By "enhance" is meant to increase proliferation of vaginal epithelial cells in such a way that can be quantitatively measured. As used herein, enhance refers to a 10% or greater (more preferably 20% or greater, and most preferably 50% or greater) increase in the total number of vaginal epithelial cells after treatment. For measurement, vaginal smears from the lateral wall of the upper third of the vagina are taken and the number of epithelial cells is determined.

By "modification" is meant any substitution of an amino acid within a peptide sequence to another, related or unrelated amino acid. Modifications can include the attachment of another structure such as a cyclic compound or other molecule to the peptide and can also include peptides that contain one or more amino acids in an altered configuration (i.e., R or S; or, L or D).

By "proliferation" is meant an increase in cell number, i.e., by mitosis of the cells. As used herein proliferation does not refer to neoplastic or abnormal cell growth.

Other features and advantages of the invention will be apparent from the following description of the preferred embodiments thereof, and from the claims.

BRIEF DESCRIPTION OF THE DRAWING

FIG. 1 is a graph showing that PTH(1-34) can stimulate vaginal cell-growth.

DETAILED DESCRIPTION OF THE INVENTION

The present invention features a method of treatment for vaginal atrophy. Peptides having at least 10% sequence identity (more preferably 50% or greater, and most preferably, 75% or greater) to HPTH or hPTHrP are chosen based on their ability to induce DNA synthesis or vaginal cell growth in vitro. These peptides are given to a patient suffering from vaginal atrophy in a dosage sufficient to enhance vaginal epithelial cell growth. An enhancement of vaginal epithelial cell growth can reverse the atrophic vaginal dryness and restore vaginal health, thus making this approach a suitable therapy for vaginal atrophy.

Synthesis and Selection of Peptides

A variety of PTH and PTHrP analogs and derivatives thereof have been made. See U.S. Pat. Nos. 4,086,196, 4,423,037, 4,771,124, 4,833,125, 4,968,669, 5,001,223, 5,087,562, 5,093,233, 5,116,952, 5,149,779, 5,171,670, 5,229,489, 5,317,010, 5,382,658, 5,393,869, 5,434,246, 5,527,772, 5,589,452, 5,807,823, 5,821,255, 5,840,690, 5,977,070, 6,025,467, 6,051,868, and 6,066,618; International Patent Application Nos. WO9402510, WO023594, and WO0031137; and EP 477,885. Methods for determining whether a particular analog is an agonist or antagonist of hPTH and hPTHrP are described in U.S. Pat. Nos. 5,527,772; 5,840,690; 6,066,618; and 6,362,163.

Peptides are available commercially as well (for example from BACHEM, Torrance, Calif.), or can be derived from commercially available peptides. Table 1 includes a list of the peptides described in this application, some of which are commercially available.

TABLE 1

| Name | Sequence | SEQ ID NO |
|---|---|---|
| hPTH | SVSEIQLMNLGKHLNSMERVEWLRKKLQDVHNFVALGAPLAPRDAGSQRP RKKEDNVLVESHEKSLGEADKADVNVLTKAKSQ | SEQ ID NO: 1 |
| rPTh | AVSEIQLMHNLGKHLASVERMQWLRKKLQDVHNFVSLFVQMAAREGSYQR PTKKEDNVLVDGNSKSLGEGDKADVDVLVKAKSQ | SEQ ID NO: 2 |
| BPTH | AVSEIQFMHNLGKHLSSMERVEWLRKKLQDVHNFVALGASLAYRDGSSQRPR KKEDNVLVESHQKSLGEADKADVDVLIKAKPQ | SEQ ID NO: 3 |
| bPTH(1-34) | AVSEIQFMHNLGKHLSSMERVEWLRKKLQDVHNF | SEQ ID NO: 4 |
| hPTH(1-34) | SVSEIQLMHNLGKHLNSMERVEWLRKKLQDVHNF | SEQ ID NO: 5 |
| bPTH(3-34) | SEIQFMHNLGKHLSSMERVEWLRKKLQDVHNF | SEQ ID NO: 6 |
| hPTH(15-34) | LNSMERVEWLRKKLQDVHNF | SEQ ID NO: 7 |
| hPTH(7-34) | LMHNLGKHLNSMERVEWLRKKLQDVHNF | SEQ ID NO: 8 |
| hPTH(5-34) | IQLMHNLGKHLNSMERVEWLRKKLQDVHNF | SEQ ID NO: 9 |
| hPTH(5-36) | IQLMHNLGKHLNSMERVEWLRKKLQDVHNFVA | SEQ ID NO: 10 |
| [Nle$^{8,18}$,Tyr$^{34}$]bPTH(1-34),Amide | AVSEIQFXHNLGKHLSSXERVEWLRKKLQDVHNY-NH$_2$ | SEQ ID NO: 11 |
| [Nle$^{8,18}$,Tyr$^{34}$]hPTH(1-34) | SVSEIQLXHNLGKHLNSXERVEWLRKKLQDVHNY | SEQ ID NO: 12 |
| [Nle$^{8,18}$,Tyr$^{34}$]bPTH(3-34),Amide | SEIQFXHNLGKHLSSXERVEWLRKKLQDVHNY-NH$_2$ | SEQ ID NO: 13 |

TABLE 1-continued

| Name | Sequence | SEQ ID NO |
|---|---|---|
| [Nle$^{8,18}$,Tyr$^{34}$]bPTH(7-34),Amide | FXHNLGKHLSSXERVEWLRKKLQDVHNY-NH$_2$ | SEQ ID NO: 14 |
| [Tyr$^{34}$]bPTH(7-34),Amide | FMHNLGKHLSSMERVEWLRKKLQDVHNY-NH$_2$ | SEQ ID NO: 15 |
| hPTHrP(1-40) | AVSEHQLLHDKGKSIQDLRRRFFLHHLIAEIHTAEIRATS | SEQ ID NO: 16 |
| hPTHrP(1-34) | AVSEHQLLHDKGKSIQDLRRRFFLHHLIAEIHTA | SEQ ID NO: 17 |
| hPTHrP(1-36) | AVSEHQLLHDKGKSIQDLRRRFFLHHLIAEIHTAEI | SEQ ID NO: 18 |
| hPTHrP(7-34) | LLHDKGKSIQDLRRRFFLHHLIAEIHTA | SEQ ID NO: 19 |
| hPTHrP(5-36) | HQLLHDKGKSIQDLRRRFFLHHLIAEIHTAEI | SEQ ID NO: 20 |
| hPTHrP(5-34) | HQLLHDKGKSIQDLRRRFFLHHLIAEIHTA | SEQ ID NO: 21 |
| hPTHrP(15-34) | IQDLRRRFFLHHLIAEIHTA | SEQ ID NO: 22 |
| [Trp$^{23}$]hPTHrP(1-36) | AVSEHQLLHDKGKSIQDLRRRFWLHHLIAEIHTAEI | SEQ ID NO: 23 |
| [Asn$^{10}$,Leu$^{11}$]hPTHrP(7-34),Amide | LLHNLGKSIQDLRRRFFLHHLIAEIHTA-NH$_2$ | SEQ ID NO: 24 |
| [Leu$^{11}$,D-Trp$^{12}$]hPTHrP(7-34),Amide | LLHDL$^D$TKSIQDLRRRFFLHHLIAEIHTA-NH$_2$ | SEQ ID NO: 25 |
| [Asn$^{10}$,Leu$^{11}$,D-Trp$^{12}$]hPTHrP(7-34),Amide | LLHNL$^D$TKSIQDLRRRFFLHHLIAEIHTA-NH$_2$ | SEQ ID NO: 26 |
| hPTHrP(7-31) | LLHDKGKSIQDLRRRFFLHHLIAEI | SEQ ID NO: 27 |
| hPTH(7-31) | LMHNLGKHLNSMERVEWLRKKLQDV | SEQ ID NO: 28 |

X = norleucine, Nle, DT = D-Trp

When selecting a candidate peptide for a method of this invention, a preferred first step is to choose a peptide which includes a fragment which has at least 10%, and more preferably 50% or greater, and most preferably 75% or greater, sequence identity with an five or greater amino acid long fragment within the amino terminal 34 amino acid region of hPTH or hPTHrP. The term "sequence identity" refers to a measure of the identity of amino acid sequences and as used herein refers to a polypeptide of at least five amino acids which has a sufficient number of amino acids identical to any of the amino acids within the amino-terminal 34 amino acids of hPTH or hPTHrP such that the total percent of identical amino acids is 10% or greater (more preferably 50% or greater and most preferably 75% or greater). For example an eight amino acid polypeptide having four amino acids that are identical to any four amino acids within the hPTH would have a 50% sequence identity with hPTH. In general, the sequences are aligned so that the highest order match is obtained. Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications.

Peptides of the present invention may also be modified in order to improve potency, bioavailability, chemical stability, and/or efficacy. For example, within one embodiment of the invention D-amino acid peptides, or retroenantio peptide sequences may be generated in order to improve the bioactivity and chemical stability of a peptide structure (see, e.g., Juvvadi et al., *J. Am. Chem. Soc.* 118: 8989-8997, 1996; Freidinger et al., *Science*, 210: 656-658, 1980). Lactam constraints (see Freidinger, supra), and/or azabicycloalkane amino acids as dipeptide surrogates can also be utilized to improve the biological and pharmacological properties of the native peptides (see, e.g., Hanessian et al., *Tetrahedron* 53:12789-12854, 1997).

Amide bond surrogates, such as thioamides, secondary and tertiary amines, heterocycles among others (see review in Spatola, A. F. in "Chemistry and Biochemistry of Amino Acids, Peptides and Proteins" Wenstein, B. Ed. Marcel Dekker, New York, 1983 Vol. 7, pp 267-357) can also be utilized to prevent enzymatic degradation of the peptide backbone thereby resulting in improved activity. Conversion of linear peptides to cyclic peptide analogs can also be utilized to improve metabolic stability, since cyclic peptides are much less sensitive to enzymatic degradation (see generally, Veber, et al. *Nature* 292:55-58, 1981).

Peptides can also be modified utilizing end group capping as esters and amides in order to slow or prevent metabolism and enhance lipophilicity. Dimers of the peptide attached by various linkers may also enhance activity and specificity (see for example: Y. Shimohigashi et al, in Peptide Chemistry 1988, Proceedings of the 26th Symposium on Peptide Chemistry, Tokyo, October 24-26, pgs. 47-50, 1989).

Suitable peptides prepared by either of the means described above may be purified using any one of several suitable means, including affinity columns, salt precipitations, anioncation exchange columns, sizing columns, and gel electrophoresis based on size and charge. Preferably, purification is accomplished using reverse-phase high-pressure liquid chromatography (HPLC).

Assays for Peptide Bioactivity

Suitable peptides, prepared as described above, may be assayed for their ability to induce proliferation by the methods described in U.S. Pat. Nos. 5,527,772 and 6,362,163, as well as by standard art-known assays for hPTHPTHrP and hPTH-2 receptor antagonist activity. For example, the peptide can be assayed for its ability to reduce the inhibition of proliferation or stimulation of differentiation in vitro of cultured human keratinocytes by hPTH(1-34), hPTHrP(1-34), or 1,25 (OH)$_2$D$_3$ as described below and in U.S. Pat. No. 5,527,772 (incorporated herein by reference).

Keratinocyte Culture

Keratinocytes are grown in culture as follows. NIH 3T3 cells are plated at $0.5 \times 10^5$ cells per 35-mm tissue-culture dish, and two days later are lethally irradiated with a cobalt-60 source (5000 rads). Keratinocytes are obtained from neonatal foreskin after overnight trypsinization at 4° C. and treatment with 0.02% EDTA. Keratinocytes are plated in 2 ml of serum-free medium per dish on the lethally irradiated 3T3 cells. Each experiment is performed on primary or secondary keratinocyte cultures obtained from different skin samples. The serum-free medium consists of Dulbecco's Modified Eagle's Medium (DMEM) with high concentration (1.8 mM) of calcium (M. A. Bioproducts, Walkersville, Md.) containing 7 growth factors: epidermal growth factor (25 ng/ml); hydrocortisone (203 ng/ml); insulin (5 µg/ml); prostaglandin E$_1$ (50 ng/ml); transferrin (5 µg/ml prostaglandin E$_1$ (50 ng/ml); cholera toxin (0.1 µg/ml); (Sigma Chemical Co., St. Louis, Mo.); and selenous acid (2 ng/ml) (Collaborative Research, Lexington, Mass.). At one week in culture, hydrocortisone and cholera toxin is removed from the medium, and the dishes are washed with 0.02% EDTA to remove any remaining 3T3 cells.

Peptides are tested, at various concentrations, in keratinocyte culture either alone or in combination with opposing peptides (i.e. agonist and antagonist peptides).

Beginning at one week in culture, groups of triplicate plates of keratinocytes are incubated with the aforementioned compounds or vehicle alone. After one week of dosing, the medium is removed from each culture and centrifuged, and the pellet is resuspended for the counting of the desquamated floater cells. A hemacytometer is used to count the different cell types under a phase-contrast microscope. The attached cells are then trypsinized for 30-40 minutes with 0.1% EDTA and 0.1% trypsin and then neutralized with medium. The keratinocytes are pelleted and resuspended in a known volume of medium. Duplicate aliquots are taken for counting the basal (small, rounded) and squamous (larger, irregular-shaped, flattened) cells. Each culture is thus evaluated for its total cell content and number of basal cells. A reduction in the inhibition of proliferation or stimulation of differentiation in vitro of cultured human keratinocytes by hPTH(1-34), hPTHrP(1-34), or 1,25(OH)$_2$D3 is considered an increase of at least 20% in the total number of cells.

Intracellular cAMP Level Measurement

The peptide can also be assayed for its ability to block cyclic AMP production. In one example, described in part by Orloff et al., (*Endocrinology* 186:3016-3028, 1995) confluent squamous carcinoma cells SqCC/Y1, are incubated for ten minutes at 37° C. with fresh DMEM media (100 µl) containing 500 µM isobutylmethylxanthine (IBMX; Sigma Chemical Co., St. Louis, Mo.). The inhibitor peptide [Leu$^{11}$, D-Trp$^{12}$]hPrP(7-34)NH$_2$ is applied to the cells in 100 µl of binding buffer two minutes prior to the addition of IBMX buffer (DMEM containing 2 mM IBMX, 1 mg/ml bovine serum albumin, 35 mM Hepes-NaOH, pH 7.4) that contains a near-maximal stimulatory dose (1.5 nM) of an agonist peptide. The cells are then incubated for 30 minutes at room temperature, the media is aspirated, and the cells are treated with 300 µl ice-cold 5% trichloroacetic acid for 15 minutes. After aspiration, an equal volume of triocytlamine-freon (25%:75%; Sigma Chemical Co.) is added to neutralize the solution. The samples are microcentrifuged for 15 minutes, supernatants are removed and cellular cAMP is measured using a commercially available radioimmunoassay (Biomedical Technologies, Stoughton, Mass.). Data are analyzed using the AssayZap software (Elsevier Science Publishers BV, Cambridge, United Kingdom).

The peptide can also be assayed for its ability to enhance cell growth in vivo using a skin punch biopsy test such as the one described in U.S. Pat. No. 5,840,690 (incorporated herein by reference). In addition, the peptide can also be assayed for its ability to induce DNA synthesis using any art-known methods for measuring DNA synthesis. For example, the measurement of incorporation of [$^3$H]thymidine into epidermal DNA in an in vivo mouse odel such as the one described below can be used to measure DNA synthesis (Holick et al., *Proc. Natl. Acad. Sci. USA,* 91:8014-8016, 1994).

DNA Synthesis

SKH-1 hairless mice, 5-6 weeks old (20-25 g; Charles River Breeding Laboratories), are fed normal mouse chow and handled in accordance with guidelines for laboratory animal care. Each mouse is given the peptide at various concentrations either alone or in combination with opposing peptides (i.e. agonist and antagonist peptides). Control mice receive only control vehicle. Peptides and vehicle are delivered intraperitoneally for three to seven days. On day three, the mice are given 45 µCi (1 µCi=37 kBq) of [$^3$H]thymidine intraperitoneally. Four hours later, mice are killed by intracervical dislocation. IN order to assay DNA synthesis in skin cells, the epidermal layer (identified by light microscopy) is scraped from the skin and DNA is extracted. To assay DNA synthesis in vaginal cells, vaginal tissue is collected and DNA is extracted. In both cases, [$^3$H]thymidine incorporation into epidermal DNA is measured and used to determine the rate of synthesis. DNA synthesis rates in the presence of agonist peptide, antagonist peptide, or both are compared. An induction of DNA synthesis is considered an increase of at least 20% in the rate of DNA synthesis in mice treated with antagonist peptide in the presence or absence of agonist peptide as compared to mice treated with only agonist peptide or control vehicle.

Peptides may also be selected based on their ability to function as an antagonist for either the hPTH/PTHrP receptor or the hPTH-2 receptor. For example, [Leu$^{11}$,D-Trp$^{12}$]hPTHrP(7-34)NH$_2$, has been shown to function as a highly potent antagonist of the hPTH/PTHrP receptor (Nutt et al., *Endocrinology* 127:491493, 1990). In addition, [Trp$^{23}$]hPTHrP (1-36) has been shown to function as a hPTH-2 receptor antagonist (U.S. Pat. No. 6,362,163 and references therein).

Pharmaceutical Compositions and Methods of Delivery

The peptides may be administered in combination with a pharmaceutically acceptable carrier substance, i.e., a carrier that is physiologically acceptable to the treated mammal while retaining the therapeutic properties of the compound with which it is administered. One exemplary pharmaceutically acceptable carrier is physiological saline. Other physiologically acceptable carriers and their formulations are known to one skilled in the art and described, for example, in Remington's Pharmaceutical Sciences, (20$^{th}$ edition), ed. A. Gennaro, 2000, Lippincott, Williams & Wilkins, Philadelphia, Pa.

The composition can be in the form of a pill, tablet, capsule, liquid, or sustained release tablet for oral administration; or a liquid for subcutaneous or parenteral administration. In addition, the compounds, can be used in a pharmacologically inert topical carrier such as one comprising a gel, a lotion, an ointment or a cream, including such carriers as water, glycerol, alcohol, propylene glycol, fatty alcohol, triglycerides, fatty acid ester or mineral oils. Other possible carriers are liquid petrolatum, isopropylpalmitate, polyethylene glycol ethanol 95%, polyoxyethylene monolaurate 5% in water, sodium lauryl sulfate 5% in water, and the like. Materials such as antioxidants, humectants, viscosity stabilizers and the like may be added, if necessary.

The peptides can be provided in the form of pharmaceutically acceptable salts. Examples of preferred salts are those of therapeutically acceptable organic acids, e.g., acetic, lactic, maleic, citric, malic, ascorbic, succinic, benzoic, salicylic, methanesulfonic, toluenesulfonic, or pamoic acid, as well as polymeric acids such as tannic acid or carboxymethyl cellulose, and salts with inorganic acids such as hydrohalic acids, e.g, hydrochloric acid, sulfuric acid, or phsophoric acid.

The peptides disclosed herein may be administered to the cervical and/or vaginal mucosa of a patient by any suitable means, but are preferably administered by a solution, gel, suspension, cream, ointment, foam, pessary, or tablet containing the peptide. Alternatively, the peptides may by administered by continuous release from a vaginal ring (Stumpf, P., *Obstet. Gynecol.* 75:9S (1990)) or an intrauterine device (Andersson, K., et al., *Obstet. Gynecol.* 79:963 (1992)).

The topical solution, gel, jelly, ointment, cream, foam, pessary, or tablet contains the peptide in a physiologically compatible vehicle, as those skilled in the art of gynecological topical delivery system development can select using conventional criteria.

Solutions formulated for administration to the vagina are usually referred to as irrigations. These are sterile solutions, prepared in a manner typical of sterile injections that are intended for prepared as a single use sterile solution.

Gels or jellies may be produced using a suitable gelling agent including, but not limited to, gelatin, tragacanth, or a cellulose derivative and may include glycerol as a humectant, emollient, and preservative.

Ointments are semi-solid preparations that consist of the active ingredient incorporated into a fatty, waxy, or synthetic base.

Examples of suitable creams include, but are not limited to, water-in-oil and oil-in-water emulsions. Water-in-oil creams may be formulated by using a suitable emulsifying agent with properties similar, but not limited, to those of the fatty alcohols such as cetyl alcohol or cetostearyl alcohol and to emulsifying wax. Oil-in-water creams may be formulated using an emulsifying agent such as cetomacrogol emulsifying wax. Suitable properties include the ability to modify the viscosity of the emulsion and both physical and chemical stability over a wide range of pH. The water soluble or miscible cream base may contain a preservative system and may also be buffered to maintain an acceptable physiological pH.

Foam preparations may be formulated to be delivered from a pressurized aerosol canister, via a suitable applicator, using inert propellants. Suitable excipients for the formulation of the foam base include, but are not limited to, propylene glycol, emulsifying wax, cetyl alcohol, and glyceryl stearate. Potential preservatives include methylparaben and propylparaben.

Pessaries are solid unit-dose forms suitably shaped for insertion into the vagina and may either be composed of a base that melts at body temperature or which dissolves when in contact with mucous secretions. Examples of suitable bases include, but are not limited to, theobroma oil, synthetic fat bases (e.g. Witepsol), polyethylene glycols (macrogols), and glycerol suppository basis.

Vaginal tablets are composed of the peptide contained within a solid dosage form base which may include, but not be limited to, excipients such as lactose, microcrystalline cellulose, corn starch, magnesium stearate, silicon dioxide, and hydroxypropyl methylcellulose.

The peptides can also be administered as part of liposomal preparations described in U.S. Pat. No. 5,260,065 (incorporated herein by reference). Such liposomes are made up of at least two distinct lipids, a primary lipid and a secondary lipid, the primary lipid constituting the greatest proportion, by weight, of any single lipid material forming the bilayers of said vesicle, the primary lipid being selected from the group consisting of $C_{12}$-$C_{18}$ fatty alcohols, $C_{12}$-$C_{18}$ glycol monoesters, $C_{12}$-$C_{18}$ glyceryl mono- and diesters, and mixtures thereof, and the primary lipid further having the property that it will to form a lipid vesicle in the absence of the secondary lipid, and the secondary lipid being present in an amount sufficient to allow formation of the lipid vesicles, the secondary lipid being selected from the group consisting of quaternary dimethyldiacyl amines, polyoxyethylene acyl alcohols, polyglycerols, sorbitan fatty acid esters, fatty acids and their salts, and mixtures thereof. The preferred methods of preparations for such liposomes are described in detail in U.S. Pat. No. 5,260,065.

The preferred primary lipids are $C_{12}$-$C_{18}$ fatty alcohols, glyceryl mono- and distearate, glyceryl dilaurate, and glycol stearate. While any of the secondary lipids could be used with any of the primary lipids, preferred combinations include polyoxyethylene 10-20 acyl alcohols or quaternary dimethyldiacyl amines as the secondary lipids to be used in conjunction with the fatty alcohols. Matching chain lengths in terms of carbon content and unsaturations is an important factor to consider for selection of the secondary lipid. These same acyl alcohols and dimethyldiacyl (specifically distearyl) amines are also useful with the glycol stearate, glyceryl monostearate, glyceryl distearate and the glyceryl dilaurate. However, the glyceryl distearate and glyceryl dilaurate may also use sodium laurate sarcosinates, as well as other matching sarcosinate salts (all being water soluble), or lauryl sarcosinates as secondary lipids.

In certain instances, primarily the stearate derivatives, a sterol such as cholesterol is a particularly useful additive. The addition of cholesterol appears to make the vesicles population more uniform in terms of size and shape. Even cholesterol is not sufficient, in itself, to allow vesicle formation. This is contrast to the materials described in U.S. Pat. No. 4,917,951 (incorporated herein by reference) which only require cholesterol to make vesicles. In certain circumstances, cholesterol will allow these materials which will not otherwise form a lamellar phase to form a lamellar phase but they cannot be formed into vesicles without the addition of the secondary lipid. In fact, some of the most preferred secondary lipids, e.g., dimethyldistearyl amine, water soluble polyoxyethylene acyl alcohols, and acyl sarcosinate salts, will not form vesicles or lamellar phases either.

According to Example 1 of U.S. Pat. No. 5,260,065, a variety of materials may be blended in order to make vesicles. Table 2 shows the composition, water uptake level, and oil uptake under hot and cold loading techniques of five different compositions. According to U.S. Pat. No. 5,260,065, none of the primary lipids used, e.g., glyceryl dilaurate (GDL), glyceryldistearate (GDS), cetyl alcohol (CA), stearyl alcohol (SA), or glycol stearate (GS) will form vesicles or lamellar phase on their own.

TABLE 2

| Composition | Water Uptake (ml/ml) | Oil Uptake (ml/ml) | |
|---|---|---|---|
| | | Hot | Cold |
| GDL/C16Q/Chol (1.0/0.05/0.05) | 13.5 | ≧7.2 | ≧2.7 |

TABLE 2-continued

| Composition | Water Uptake (ml/ml) | Oil Uptake (ml/ml) Hot | Oil Uptake (ml/ml) Cold |
|---|---|---|---|
| GDS/POE10SA/Chol (1.0/0.5/0.25) | 12.5 | ≧6.9 | ≧6.5 |
| CA/POE10CA/Chol (1.0/0.2/0.1) | 9.5 | ≧4.2 | ≧4.2 |
| SA/C18Q/Chol (1.0/0.2/0.1) | 13.5 | ≧6.5 | ≧6.5 |
| GS/POE10SA/Chol (1.0/0.2/0.1) | 13.5 | ≧6.5 | ≧6.5 |

The first compound shown in Table 2 is a blend of glyceryl dilaurate, dimethyldicetyl quaternary amine (C16Q), and cholesterol (Chol) in a 1.0:0.05:0.05 molar ratio. According to U.S. Pat. No. 5,260,065, the water uptake is 13.5 ml/ml of lipid and the hot load and cold loading values were ≧7.2 and ≧2.7 ml of oil/ml of lipid, respectively. According to U.S. Pat. No. 5,260,065, the vesicles were made by blending the two lipids and the cholesterol at 70-75° C. with the aqueous phase at 65° C. According to U.S. Pat. No. 5,260,065, the lipid phase was placed in one syringe, the aqueous phase was placed in another syringe, and the two syringes were connected by a stopcock. According to U.S. Pat. No. 5,260,065, the material was shear mixed by blending from one syringe to another through the stopcock forming vesicles in less than two minutes. According to U.S. Pat. No. 5,260,065, for the cold loading technique, the preformed vesicles were mixed with 20% and 50% V/V mineral oil (Drakeol 19) using the same syringe technique to load the oil. According to U.S. Pat. No. 5,260,065, for the hot loading technique, the oil was heated to 70-75° C., blended with the lipophilic phase prior to hydration by the aqueous phase, and then the combined lipophilic/water immiscible oily phase was hydrated by the aqueous phase. According to U.S. Pat. No. 5,260,065, either hot loading or cold loading techniques may be used for a mineral oil but with a highly volatile oil which would not survive the 70-75° C. heating, the cold loading technique, which can be carried out a ambient temperature, is preferred.

According to U.S. Pat. No. 5,260,065, the second compounded tested was a blend of glyceryl distearate, Polyoxyethylene 10 stearyl alcohol (POE10SA), and cholesterol in a 1.0:0.5:0.25 molar ratio. This blended material had a water uptake of 12.5 ml/ml lipid and the oil uptake for either hot and cold loading was >6.5 ml/ml using the same techniques previously described.

According to U.S. Pat. No. 5,260,065, the third material tested was a blend of cetyl alcohol, polyoxyethylene 10 cetyl alcohol (POE10CA), and cholesterol in a 1:0.2:0.1 molar ratio. Water uptake was 9.5 ml/ml and both hot and cold oil uptake was >4.2 ml/ml lipid.

According to U.S. Pat. No. 5,260,065, the fourth combination tested was a blend of stearyl alcohol, dimethyldistearyl quaternary amine (C18Q), and cholesterol on a 1:0.2:0.1 ratio. Water uptake was 13.5 ml/ml and oil uptake on both a hot and cold basis was >6.5 ml/ml lipid.

According to U.S. Pat. No. 5,260,065, the fifth compound tested was a blend of glycol stearate, polyoxyethylene 10 stearyl alcohol, and cholesterol in a 1:0.2:0.1 ratio. Again, the water uptake was approximately 13.5 ml/ml and the oil uptake was >6.5 ml/ml under both hot and cold loading techniques.

According to Example 2 of U.S. Pat. No. 5,260,065, retinoic acid, a water insoluble material in a water immiscible carrier, was used in lieu of the mineral oil of Example 1 in the amorphous central cavity of the paucilamellar lipid vesicles. Retinoic acid has a substantial number of dermatological uses including, potentially, the reduction of facial wrinkles.

TABLE 3

|  | A | B |
|---|---|---|
| Cetyl Alcohol | 4.7 g |  |
| Glycol Stearate |  | 11.5 g |
| POE10 Cetyl Alcohol | 2.35 g |  |
| POE10 Stearyl Alcohol |  | 2.3 g |
| Cholesterol | 1.2 g | 1.15 g |
| Petrolatum | 10.9 g |  |
| Paraffin Wax | 11.6 g |  |
| Soybean Oil |  | 21.8 g |
| Retinoic Acid | 0.25 g | 0.25 g |
| Deionized Water | 69 g | 63 g |

According to U.S. Pat. No. 5,260,065, Table 3 shows the formulas for two different retinoic acid formulations, one using a cetyl alcohol/polyoxyethylene 10 cetyl alcohol blend and the other using a glycol stearate/polyoxyethylene 10 stearyl alcohol blend as the vesicles formers. According to U.S. Pat. No. 5,260,065, both formulas include cholesterol while one uses a mixture petrolatum and paraffin wax as a carrier for the retinoic acid while the other uses a soybean oil carrier. According to U.S. Pat. No. 5,260,065, in both cases, the retinoic acid was dissolved in the carrier at 65-75° C. According to U.S. Pat. No. 5,260,065, the lipids and the cholesterol were then heated and blended to homogeneity and the retinoic acid mixture was added and blended therein. According to U.S. Pat. No. 5,260,065, an aqueous phase consisting of the deionized water was then heated to approximately 65° C. and the resulting phases were shear mixed to form the vesicles. According to U.S. Pat. No. 5,260,065, while the syringe method described in Example 1 could be used, a NovaMix™ vesicle forming machine manufactured by Micro Vesicular Systems, Inc., Nashua, N.H. was used. This machine, which is described in more detail in U.S. Pat. No. 4,895,452 (incorporated herein by reference), has a substantially cylindrical central chamber with an axial outflow tube and tangentially located inflow tubes. According to U.S. Pat. No. 5,260,065, the phases are injected into the central chamber, under pressure sufficient to form turbulent flow and shear mixing, rapid vesicle formation occurs, and the vesicles are removed through the outflow tube.

Alternatively, the apparatus described in U.S. Pat. No. 5,013,497 (incorporated herein by reference) may be used to prepare the liposomes.

According to Example 3 of U.S. Pat. No. 5,260,065, two different, formulations for encapsulating anthralin, an antipsoriatic, were tested. Table 4 lists the ingredients used in these formulations. According to the present invention, a PTH peptide analog may be substituted for anthralin.

TABLE 4

|  | C | D |
|---|---|---|
| Glyceryl Distearate | 9.4 g |  |
| Cetyl Alcohol |  | 6.85 g |
| Dimethyl Distearyl Ammonium Chloride | 0.3 g |  |
| POE10 Cetyl Alcohol |  | 1.35 g |
| Sodium Lauryl Sarcosinate | 1.4 g |  |
| Cholesterol | 1.0 g | 0.7 g |
| Petrolatum | 15.7 g | 17.3 g |
| Paraffin Wax | 16.8 g | 18.5 g |
| Anthralin | 0.5 g | 0.5 g |
| Deionized Water | 54.9 g | 54.8 g |

According to U.S. Pat. No. 5,260,065, in formulation C, the petrolatum and paraffin are melted together and the anthralin is dissolved into the carrier mixture. According to U.S. Pat. No. 5,260,065, this also the case of formulation D. According to U.S. Pat. No. 5,260,065, this petrolatum/paraffin wax mixture appears to be particularly advantageous in that microcrystals form rather than the macroscopic crystals which normally appear when anthralin cools. According to U.S. Pat. No. 5,260,065, in formulation C, however, the glyceryl distearate, cholesterol and dimethyldistearyl ammonium chloride are blended together at approximately 75° C. until clear and the anthralin solution (forming a water immiscible phase) is then mixed therein. According to U.S. Pat. No. 5,260,065, the aqueous phase is formed by heating the deionized water to approximately 65° C. and dissolving the secondary lipid, the sodium lauryl sarcosinate, therein. According to U.S. Pat. No. 5,260,065, the aqueous phase and the lipid phase are then shear mixed, using a NovaMix™ machine as described in Example 2, to form vesicles. According to U.S. Pat. No. 5,260,065, in contrast, in formulation D, the cetyl alcohol, polyoxyethylene 10 cetyl alcohol and the cholesterol are blended together at an elevated temperature, the anthralin solution is mixed in, and the aqueous which consists merely of the deionized water is shear mixed using the NovaMix™ machine to form the vesicles. According to U.S. Pat. No. 5,260,065, the difference in the procedure is that the nonionic lipids of formulation D cannot be carried in the aqueous solution as is the ionic sodium lauryl sarcosinate of formulation C. According to U.S. Pat. No. 5,260,065, either formulation forms acceptable anthralin carrying vesicles.

According to Example 4 of U.S. Pat. No. 5,260,065, three different materials, Vitamin E acetate, levamisole base, and a butter flavor oil were carried in the central cavity of vesicles of the invention. Table 5 shows the formulas for these vesicles. According to the present invention, a PTH peptide analog may be substituted for vitamin E acetate.

TABLE 5

|  | E | F | G |
|---|---|---|---|
| Glyceryl Distearate | 11.2 g |  | 4.35 g |
| Glycol Stearate |  | 7.5 g |  |
| POE10 Stearyl Alcohol | 5.6 g | 1.5 g | 2.2 g |
| Cholesterol | 2.8 g | 0.75 g | 1.1 g |
| Soybean Oil |  | 8.5 g |  |
| Vitamin E | 2.2 g |  |  |
| Levamisole Base |  | 4.63 g |  |
| Butter Flavor Oil |  |  | 20.0 g |
| Deionized Water | 78.2 g | 74.12 g | 72.35 g |

According to U.S. Pat. No. 5,260,065, formulation E uses glyceryl distearate, polyoxyethylene 10 stearyl alcohol, and cholesterol as the lipophilic phase which are blended at 70° C. to obtain a clear, homogeneous solution. According to U.S. Pat. No. 5,260,065, the Vitamin E acetate was dissolved therein and the mixture was hydrated with 65° C. water using the NovaMix™ machine as described in Example 2.

According to U.S. Pat. No. 5,260,065, formulation F used a levamisole base (a sheep dip) in soybean oil at 75° C. to form the water immiscible phase. According to U.S. Pat. No. 5,260, 065, the glycol stearate, polyoxyethylene stearyl alcohol and cholesterol were heated together at 75° C. to obtain a clear, homogeneous solution and the levamisole/soybean oil mixture was blended therewith. According to U.S. Pat. No. 5,260, 065, the deionized water was heated to approximately 65° C. and used as a hydrating solution for the lipids, again using the previously described NovaMix™ machine.

According to U.S. Pat. No. 5,260,065, in formulation G, the lipids and cholesterol were melted together at 75° C. and the buffer oil dissolved therein. According to U.S. Pat. No. 5,260,065, again, the deionized water was heated to approximately 65° C. and used as a hydrating solution in a NovaMix™ machine.

According to Example 5 of U.S. Pat. No. 5,260,065, three different formulations for vesicles using retinoic acid, with both cationic and anionic vesicles may be used. Table 6 lists the formulations for each vesicle. According to the present invention, a PTH peptide analog may be substituted for retinoic acid.

TABLE 6

|  | H | I | J |
|---|---|---|---|
| Glyceryl Distearate | 9.4 g |  |  |
| Glycol Stearate |  | 13.2 g | 13.2 g |
| Dimethyl Distearyl Ammonium Chloride | 0.3 g |  |  |
| Dimethyl Dicetyl Ammonium Chloride |  | 0.6 g |  |
| Sodium Oleate |  |  | 1.0 g |
| Petrolatum | 15.7 g |  |  |
| Paraffin Wax | 16.8 g |  |  |
| Soybean Oil |  | 22.0 g | 22.0 g |
| Retinoic Acid | 0.25 g | 0.25 g | 0.25 g |
| Deionized Water | 56.55 g | 62.75 g | 63.35 g |

According to U.S. Pat. No. 5,260,065, formulation H uses the paraffin wax/petrolatum carrier for the retinoic acid, with the retinoic acid being dissolved in the carrier at approximately 65-75° C. According to U.S. Pat. No. 5,260,065, the lipophilic phase is formed of glyceryl distearate, cholesterol, and the dimethyl distearyl ammonium chloride. According to U.S. Pat. No. 5,260,065, the carrier containing the retinoic acid is blended into the lipophilic phase and is hydrated with the deionized water using the NovaMix™ machine as described in Example 2.

According to U.S. Pat. No. 5,260,065, formulations I and J use the soybean oil carrier and the same materials except for the secondary lipid. According to U.S. Pat. No. 5,260,065, in formulation I, the secondary lipid, which forms part of the initial lipophilic phase, is dimethyl dicetyl ammonium chloride while in formulation J, the secondary lipid, which is incorporated into the aqueous phase, is sodium oleate. According to U.S. Pat. No. 5,260,065, in either case, the retinoic acid is dissolved in the soybean oil at elevated temperatures, the soybean oil is blended into the lipophilic phase, and the combined phase is then hydrated using the aqueous phase. According to U.S. Pat. No. 5,260,065, formulation J forms anionic vesicles while formulation I forms cationic vesicles. However, according to U.S. Pat. No. 5,260,065, both are effective in encapsulating the retinoic acid.

The liposome encapsulated peptides can be admixed with a pharmacologically inert topical carrier such as one comprising a gel, an ointment or a cream, including such carriers as water, glycerol, alcohol, propylene glycol, fatty alcohol, triglycerides, fatty acid ester or mineral oils. Other possible carriers are liquid petrolatum, isopropylpalmitate, polyethylene glycol ethanol 95%, polyoxyethylene monolaurate 5% in water, sodium lauryl sulfate 5% in water, and the like. Materials such as antioxidants, humectants, viscosity stabilizers and the like may be added, if necessary.

To promote the penetration and utilization of the peptide, any of the forgoing formulations can further include a zinc salt. Suitable zinc salts include water-soluble organic salts having relatively low molecular weights (including zinc acetate, butyrate, gluconate, glycerate, glycolate, lactate, propionate, ascorbate, citrate, aspartate, picolinate, orotate, etc.). Highly ionizing zinc salts, such as chloride, bromide, oxide, bisulfate, sulfate, bicarbonate, carbonate, nitrate, or combinations thereof, can also be used. Preferred zinc salt concentrations in the formulations described herein are in the range of 0.03% to about 5% or about 0.5% to about 30% w/v, depending upon the formula weight of the salt.

Kits

A kit containing therapeutically effective amounts of hPTH(1-34), hPTHrP(1-34), hPTH(7-34), hPTHrP(7-34), or a PTH analog that is related to PTH and is capable of reducing the inhibition of proliferation or stimulation of differentiation in vitro of cultured human keratinocytes by hPTH(1-34), hPTHrP(1-34), (SEQ ID NOs: 5, 17) or 1,25(OH)$_2$D3 in a dosage sufficient to enhance vaginal epithelial cell growth is used for the treatment of vaginal atrophy. Alternatively, the kit can contain a PTh peptide analog that is at least five amino acids long, has at least 10% sequence identity with a sequence within the 34 amino acid N-terminal region of hPTH or hPTHrP, and is capable of inducing DNA synthesis or enhancing skin cell or vaginal cell growth in vivo. The kit also includes an applicator for the topical application of the peptide to the vulvovaginal area or for intravaginal or intracervical application.

Use and Dosage

The peptides are administered in therapeutically effective amounts to a patient suffering from vaginal atrophy in an amount sufficient to enhance vaginal epithelial cell growth.

For topical administration, the peptides are formulated for direct application to an area. Conventional forms for this purpose include gels, creams, ointments, lotions, suppositories, pastes, jellies, sprays, and aerosols. The percent by weight of a peptide of the invention present in a topical formulation will depend on various factors, but generally ranges from 0.001% to 95% of the total weight of the formulation, and typically 0.005-5% by weight.

Oral dosage is dependent upon the age, health, and weight of the recipient; kind of concurrent treatment, if any; frequency of treatment; and the nature of the effect desired. Generally, daily dosage ranges from about 0.001 µg/kg to 10,000 µg/kg, preferably 0.01 µg/kg to 1000 µg/kg, and most preferably 0.1 to 10 µg/kg of body weight. Normally, from 0.1 to 1000 µg/kg per day, in one or more applications per day, is effective to obtain the desired results.

The topical application of zinc oxide cream to the vulvovaginal region can also be administered prior to administering the peptide in order to help retain moisture in the region.

The therapeutic effectiveness of the peptide is determined by its ability to enhance vaginal epithelial cell growth. One possible test for effectiveness is described in the following example.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Example 1

Test for the Efficacy of Peptide Hormone Treatment for Vaginal Atrophy

Women suffering from vaginal atrophy associated with menopause are selected. These women are in general good health. These patients are asked to keep a daily log noting such details as vaginal itching and scaling and the degree of comfort in sexual intercourse. These women are placed on a clinical protocol of receiving 20-100 mg of a compound of this invention by oral administration either as a single or split dose. Alternatively, these patients are placed in a protocol for topical administration using a suitable formulation containing 5-50% (by weight) of an active compound of this invention applied to the affected area once or twice a day. Either of these protocols continues for two to twelve months. Subsequent evaluations, both quantitative and qualitative, are made at appropriate intervals. A positive result is an improvement in the comfort of sexual intercourse and/or a decrease in vaginal itching or scaling.

Gynecologic exams are also performed to evaluate effectiveness. Each woman undergoes a gynecologic exam before beginning the treatment regimen and is evaluated again at appropriate intervals. The examination tests for vaginal pH and a positive result is seen in a lowering of the vaginal pH. Vaginal cytology is also evaluated using smears taken from the lateral vaginal wall. A positive result is a 10% or greater increase (more preferably 20% or greater and most preferably 50% or greater) increase in the number of epithelial cells. The number of parabasal, intermediate, and superficial cells is counted and a mean maturation index is calculated. A 10% or greater increase in the number of superficial cells is also considered a positive result.

Example 2

The vaginas from five SKH-1 hairless mice were harvested, washed, and placed in trypsin 1× overnight. From each, the vaginal epithelium was peeled and rinsed in 0.02% EDTA solution and centrifuged to isolate the cells. The cells were rinsed in media, centrifuged, and plated into a 100 mm dish atop a layer of irradiated 3T3 cells containing media as is used for keratinocytes and described above. The cells were grown and passed into 24 well plates for tritiated thymidine incorporation as described above. Cells were treated with either a placebo vehicle or with $1\times10^{-7}$ M PTH(1-34) for 24 hours. The cells were harvested and the DNA was extracted and counted using a beta liquid scintillation counter. The amount of tritiated thymidine recovered in the DNA is a measure of DNA synthesis in the cells and is synonymous with cellular proliferative activity. As shown in FIG. 1, there was increased incorporation of tritiated thymidine into the DNA of the mouse vaginal cells that were treated with PTH (1-34). This result shows that PTH(1-34) can stimulate vaginal cell growth.

Other Embodiments

From the foregoing description, it is apparent that variations and modifications may be made to the invention described herein to adopt it to various usages and conditions. Such embodiments are also within the scope of the following claims.

All publications mentioned in this specification are herein incorporated by reference to the same extent as if each independent publication or patent application was specifically and individually indicated to be incorporated by the reference.

What is claimed is:

1. A method of treating vaginal atrophy in a human patient comprising administering to the patient the peptide hPTH (1-34) (SEQ ID NO: 5), hPTHrP (1-34) (SEQ ID NO: 17), hPTH (7-34) (SEQ ID NO: 8), hPTHrP (7-34) (SEQ ID NO: 19), hPTH (7-31) (SEQ ID NO: 28), hPTH (5-34) (SEQ ID NO: 9), hPTH (5-36) (SEQ ID NO: 10), [Nle$^{8,18}$, Tyr$^{34}$] bPTH (7-34) NH2 (SEQ ID NO: 14), [Tyr$^{34}$] bPTH (7-34) NH2 (SEQ ID NO: 15), hPTHrP (7-31) (SEQ ID NO: 29), hPTHrP (5-36) (SEQ ID NO: 20), or hPTHrP (5-34) (SEQ ID NO: 21) in a dosage sufficient to enhance vaginal epithelial cell growth, wherein the peptide is capable of inducing DNA synthesis or vaginal cell growth in vitro.

2. A method of treating vaginal atrophy in a human patient comprising administering to the patient the peptide hPTH (1-34) (SEQ ID NO: 5), hPTHrP (1-34) (SEQ ID NO: 17), hPTH (7-34) (SEQ ID NO: 8), hPTHrP (7-34) (SEQ ID NO: 19), hPTH (7-31) (SEQ ID NO: 28), hPTH (5-34) (SEQ ID NO: 9), hPTH (5-36) (SEQ ID NO: 10), [Nle$^{8,18}$, Tyr$^{34}$] bPTH (7-34) NH2 (SEQ ID NO: 14), [Tyr$^{34}$] bPTH (7-34) NH2 (SEQ ID NO: 15), hPTHrP (7-31) (SEQ ID NO: 29), hPTHrP (5-36) (SEQ ID NO: 20), or hPTHrP (5-34) (SEQ ID NO: 21), wherein the peptide is capable of inducing DNA synthesis or vaginal cell growth in vivo.

3. The method of claim 1 or 2, wherein said peptide is at least eight amino acids long.

4. The method of claim 1 or 2, wherein said peptide is hPTH (7-31) (SEQ ID NO: 28), hPTH (5-34) (SEQ ID NO: 9), hPTH (5-36) SEQ ID NO: 10), [Nle$^{8,18}$, Tyr$^{34}$] bPTH (7-34) NH2 (SEQ ID NO: 14), [Tyr$^{34}$] bPTH (7-34) NH2 (SEQ ID NO: 15), hPTHrP (7-31) (SEQ ID NO: 29), hPTHrP (5-36) (SEQ ID NO: 20), or hPTHrP (5-34) (SEQ ID NO: 21).

5. The method of claim 1 or 2, wherein said peptide is a cyclic peptide.

6. The method of claim 1 or 2, wherein said peptide is administered vulvovaginally, intravaginally, intracervically, subcutaneously, or orally.

7. The method of claim 1 or 2, further comprising the step of topically administering zinc oxide cream to the vulva of said patient.

8. The method of claim 1 or 2, wherein said peptide is combined with a pharmaceutically acceptable carrier substance.

9. The method of claim 1 or 2, wherein said peptide is encapsulated within a liposome, which comprises at least two distinct lipids, a primary lipid and a secondary lipid, the primary lipid constituting the greatest proportion, by weight, of any single lipid material forming the bilayers of said vesicle, the primary lipid being selected from the group consisting of $C_{12}$-$C_{18}$ fatty alcohols, $C_{12}$-$C_{18}$ glycol monoesters, $C_{12}$-$C_{18}$ glyceryl mono- and diesters, and mixtures thereof, and the primary lipid further having the property that it will form a lipid vesicle in the absence of the secondary lipid, and the secondary lipid being present in an amount sufficient to allow formation of the lipid vesicles, the secondary lipid being selected from the group consisting of quaternary dimethyldiacyl amines, polyoxyethylene acyl alcohols, polyglycerols, sorbitan fatty acid esters, fatty acids and their salts, and mixtures thereof.

10. The method of claim 1 or 2, wherein said peptide is administered as a solution, a gel, a suspension, a cream, an ointment, a foam, a pessary, or a tablet.

11. The method of claim 1 or 2, wherein said peptide is administered in combination with a zinc salt.

12. The method of claim 1 or 2, wherein the peptide is administered in the form of a pharmaceutically acceptable salt.

* * * * *

SEQUENCE LISTING

<160> NUMBER OF SEQ ID NOS: 29

<210> SEQ ID NO 1
<211> LENGTH: 84
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 2
<211> LENGTH: 84
<212> TYPE: PRT
<213> ORGANISM: rabbitt

<400> SEQUENCE: 2

Ala Val Ser Glu Ile Gln Leu Met His Asn Leu Gly Lys His Leu Ala
1               5                   10                  15

Ser Val Glu Arg Met Gln Trp Leu Arg Lys Lys Leu Gln Asp Val His
            20                  25                  30

Asn Phe Val Ser Leu Gly Val Gln Met Ala Ala Arg Glu Gly Ser Tyr
        35                  40                  45

Gln Arg Pro Thr Lys Lys Glu Asp Asn Val Leu Val Asp Gly Asn Ser
    50                  55                  60

Lys Ser Leu Gly Glu Gly Asp Lys Ala Asp Val Asp Val Leu Val Lys
65                  70                  75                  80

Ala Lys Ser Gln

<210> SEQ ID NO 3
<211> LENGTH: 84
<212> TYPE: PRT
<213> ORGANISM: Bovine

<400> SEQUENCE: 3

Ala Val Ser Glu Ile Gln Phe Met His Asn Leu Gly Lys His Leu Ser
1               5                   10                  15

Ser Met Glu Arg Val Glu Trp Leu Arg Lys Lys Leu Gln Asp Val His
            20                  25                  30

Asn Phe Val Ala Leu Gly Ala Ser Ile Ala Tyr Arg Asp Gly Ser Ser
        35                  40                  45

Gln Arg Pro Arg Lys Lys Glu Asp Asn Val Leu Val Glu Ser His Gln
    50                  55                  60

Lys Ser Leu Gly Glu Ala Asp Lys Ala Asp Val Asp Val Leu Ile Lys
65                  70                  75                  80

Ala Lys Pro Gln

<210> SEQ ID NO 4
<211> LENGTH: 34
<212> TYPE: PRT
<213> ORGANISM: Bovine

<400> SEQUENCE: 4

Ala Val Ser Glu Ile Gln Phe Met His Asn Leu Gly Lys His Leu Ser
1               5                   10                  15

Ser Met Glu Arg Val Glu Trp Leu Arg Lys Lys Leu Gln Asp Val His
            20                  25                  30

Asn Phe

<210> SEQ ID NO 5
<211> LENGTH: 34
<212> TYPE: PRT
<213> ORGANISM: Homo sapiens

<400> SEQUENCE: 5

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 6
<211> LENGTH: 32
<212> TYPE: PRT
<213> ORGANISM: Bovine

<400> SEQUENCE: 6

Ser Glu Ile Gln Phe Met His Asn Leu Gly Lys His Leu Ser Ser Met
1               5                   10                  15

Glu Arg Val Glu Trp Leu Arg Lys Lys Leu Gln Asp Val His Asn Phe
            20                  25                  30

<210> SEQ ID NO 7
<211> LENGTH: 20
<212> TYPE: PRT
<213> ORGANISM: Homo sapiens

<400> SEQUENCE: 7

Leu Asn Ser Met Glu Arg Val Glu Trp Leu Arg Lys Lys Leu Gln Asp
1               5                   10                  15

Val His Asn Phe
            20

<210> SEQ ID NO 8
<211> LENGTH: 28
<212> TYPE: PRT
<213> ORGANISM: Homo sapiens

<400> SEQUENCE: 8

Leu Met His Asn Leu Gly Lys His Leu Asn Ser Met Glu Arg Val Glu
1               5                   10                  15

Trp Leu Arg Lys Lys Leu Gln Asp Val His Asn Phe
            20                  25

<210> SEQ ID NO 9
<211> LENGTH: 30
<212> TYPE: PRT
<213> ORGANISM: Homo sapiens

<400> SEQUENCE: 9

```
Ile Gln Leu Met His Asn Leu Gly Lys His Leu Asn Ser Met Glu Arg
1               5                   10                  15

Val Glu Trp Leu Arg Lys Lys Leu Gln Asp Val His Asn Phe
            20                  25                  30
```

<210> SEQ ID NO 10
<211> LENGTH: 32
<212> TYPE: PRT
<213> ORGANISM: Homo sapiens

<400> SEQUENCE: 10

```
Ile Gln Leu Met His Asn Leu Gly Lys His Leu Asn Ser Met Glu Arg
1               5                   10                  15

Val Glu Trp Leu Arg Lys Lys Leu Gln Asp Val His Asn Phe Val Ala
            20                  25                  30
```

<210> SEQ ID NO 11
<211> LENGTH: 34
<212> TYPE: PRT
<213> ORGANISM: Bovine
<220> FEATURE:
<221> NAME/KEY: VARIANT
<222> LOCATION: (8)..(18)
<223> OTHER INFORMATION: Xaa = Nle
<220> FEATURE:
<221> NAME/KEY: AMIDATION
<222> LOCATION: (34)..(34)
<223> OTHER INFORMATION: Tyrosine at position 34 is amidylated

<400> SEQUENCE: 11

```
Ala Val Ser Glu Ile Gln Phe Xaa His Asn Leu Gly Lys His Leu Ser
1               5                   10                  15

Ser Xaa Glu Arg Val Glu Trp Leu Arg Lys Lys Leu Gln Asp Val His
            20                  25                  30

Asn Tyr
```

<210> SEQ ID NO 12
<211> LENGTH: 34
<212> TYPE: PRT
<213> ORGANISM: Homo sapiens
<220> FEATURE:
<221> NAME/KEY: VARIANT
<222> LOCATION: (8)..(18)
<223> OTHER INFORMATION: Xaa = Nle

<400> SEQUENCE: 12

```
Ser Val Ser Glu Ile Gln Leu Xaa His Asn Leu Gly Lys His Leu Asn
1               5                   10                  15

Ser Xaa Glu Arg Val Glu Trp Leu Arg Lys Lys Leu Gln Asp Val His
            20                  25                  30

Asn Tyr
```

<210> SEQ ID NO 13
<211> LENGTH: 32
<212> TYPE: PRT
<213> ORGANISM: Bovine
<220> FEATURE:
<221> NAME/KEY: VARIANT
<222> LOCATION: (6)..(16)
<223> OTHER INFORMATION: Xaa = Nle
<220> FEATURE:
<221> NAME/KEY: AMIDATION
<222> LOCATION: (32)..(32)
<223> OTHER INFORMATION: Tyrosine at position 32 is amidylated

<400> SEQUENCE: 13

```
Ser Glu Ile Gln Phe Xaa His Asn Leu Gly Lys His Leu Ser Xaa
1               5                   10                  15

Glu Arg Val Glu Trp Leu Arg Lys Lys Leu Gln Asp Val His Asn Tyr
                20                  25                  30
```

<210> SEQ ID NO 14
<211> LENGTH: 28
<212> TYPE: PRT
<213> ORGANISM: Bovine
<220> FEATURE:
<221> NAME/KEY: VARIANT
<222> LOCATION: (2)..(12)
<223> OTHER INFORMATION: Xaa = Nle
<220> FEATURE:
<221> NAME/KEY: AMIDATION
<222> LOCATION: (28)..(28)
<223> OTHER INFORMATION: Tyrosine at position 28 is amidylated

<400> SEQUENCE: 14

```
Phe Xaa His Asn Leu Gly Lys His Leu Ser Ser Xaa Glu Arg Val Glu
1               5                   10                  15

Trp Leu Arg Lys Lys Leu Gln Asp Val His Asn Tyr
                20                  25
```

<210> SEQ ID NO 15
<211> LENGTH: 28
<212> TYPE: PRT
<213> ORGANISM: Bovine
<220> FEATURE:
<221> NAME/KEY: AMIDATION
<222> LOCATION: (28)..(28)
<223> OTHER INFORMATION: Tyrosine at position 28 is amidylated

<400> SEQUENCE: 15

```
Phe Met His Asn Leu Gly Lys His Leu Ser Ser Met Glu Arg Val Glu
1               5                   10                  15

Trp Leu Arg Lys Lys Leu Gln Asp Val His Asn Tyr
                20                  25
```

<210> SEQ ID NO 16
<211> LENGTH: 40
<212> TYPE: PRT
<213> ORGANISM: Homo sapiens

<400> SEQUENCE: 16

```
Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
                20                  25                  30

Thr Ala Glu Ile Arg Ala Thr Ser
                35                  40
```

<210> SEQ ID NO 17
<211> LENGTH: 34
<212> TYPE: PRT
<213> ORGANISM: Homo sapiens

<400> SEQUENCE: 17

```
Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
                20                  25                  30

Thr Ala
```

```
<210> SEQ ID NO 18
<211> LENGTH: 36
<212> TYPE: PRT
<213> ORGANISM: Homo sapiens

<400> SEQUENCE: 18

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile
        35

<210> SEQ ID NO 19
<211> LENGTH: 28
<212> TYPE: PRT
<213> ORGANISM: Homo sapiens

<400> SEQUENCE: 19

Leu Leu His Asp Lys Gly Lys Ser Ile Gln Asp Leu Arg Arg Arg Phe
1               5                   10                  15

Phe Leu His His Leu Ile Ala Glu Ile His Thr Ala
            20                  25

<210> SEQ ID NO 20
<211> LENGTH: 32
<212> TYPE: PRT
<213> ORGANISM: Homo sapiens

<400> SEQUENCE: 20

His Gln Leu Leu His Asp Lys Gly Lys Ser Ile Gln Asp Leu Arg Arg
1               5                   10                  15

Arg Phe Phe Leu His His Leu Ile Ala Glu Ile His Thr Ala Glu Ile
            20                  25                  30

<210> SEQ ID NO 21
<211> LENGTH: 30
<212> TYPE: PRT
<213> ORGANISM: Homo sapiens

<400> SEQUENCE: 21

His Gln Leu Leu His Asp Lys Gly Lys Ser Ile Gln Asp Leu Arg Arg
1               5                   10                  15

Arg Phe Phe Leu His His Leu Ile Ala Glu Ile His Thr Ala
            20                  25                  30

<210> SEQ ID NO 22
<211> LENGTH: 20
<212> TYPE: PRT
<213> ORGANISM: Homo sapiens

<400> SEQUENCE: 22

Ile Gln Asp Leu Arg Arg Arg Phe Phe Leu His His Leu Ile Ala Glu
1               5                   10                  15

Ile His Thr Ala
            20

<210> SEQ ID NO 23
<211> LENGTH: 36
<212> TYPE: PRT
<213> ORGANISM: Homo sapiens

<400> SEQUENCE: 23
```

```
Ala Val Ser Glu His Gln Leu Leu His Asp Lys Gly Lys Ser Ile Gln
1               5                   10                  15

Asp Leu Arg Arg Arg Phe Trp Leu His His Leu Ile Ala Glu Ile His
                20                  25                  30

Thr Ala Glu Ile
            35

<210> SEQ ID NO 24
<211> LENGTH: 28
<212> TYPE: PRT
<213> ORGANISM: Homo sapiens
<220> FEATURE:
<221> NAME/KEY: AMIDATION
<222> LOCATION: (28)..(28)
<223> OTHER INFORMATION: Ala at position 28 is amidylated

<400> SEQUENCE: 24

Leu Leu His Asn Leu Gly Lys Ser Ile Gln Asp Leu Arg Arg Arg Phe
1               5                   10                  15

Phe Leu His His Leu Ile Ala Glu Ile His Thr Ala
                20                  25

<210> SEQ ID NO 25
<211> LENGTH: 28
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Thr at position 6 is a D-isomer
<220> FEATURE:
<221> NAME/KEY: AMIDATION
<222> LOCATION: (28)..(28)
<223> OTHER INFORMATION: Ala at position 28 is amidylated

<400> SEQUENCE: 25

Leu Leu His Asp Leu Thr Lys Ser Ile Gln Asp Leu Arg Arg Arg Phe
1               5                   10                  15

Phe Leu His His Leu Ile Ala Glu Ile His Thr Ala
                20                  25

<210> SEQ ID NO 26
<211> LENGTH: 28
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Thr at position 6 is a D-isomer
<220> FEATURE:
<221> NAME/KEY: AMIDATION
<222> LOCATION: (28)..(28)
<223> OTHER INFORMATION: Ala at position 28 is amidylated

<400> SEQUENCE: 26

Leu Leu His Asn Leu Thr Lys Ser Ile Gln Asp Leu Arg Arg Arg Phe
1               5                   10                  15

Phe Leu His His Leu Ile Ala Glu Ile His Thr Ala
                20                  25

<210> SEQ ID NO 27
<211> LENGTH: 25
<212> TYPE: PRT
<213> ORGANISM: Homo sapiens

<400> SEQUENCE: 27
```

```
Leu Leu His Asp Lys Gly Lys Ser Ile Gln Asp Leu Arg Arg Arg Phe
1               5                   10                  15

Phe Leu His His Leu Ile Ala Glu Ile
            20              25

<210> SEQ ID NO 28
<211> LENGTH: 25
<212> TYPE: PRT
<213> ORGANISM: Homo sapiens

<400> SEQUENCE: 28

Leu Met His Asn Leu Gly Lys His Leu Asn Ser Met Glu Arg Val Glu
1               5                   10                  15

Trp Leu Arg Lys Lys Leu Gln Asp Val
            20              25

<210> SEQ ID NO 29
<211> LENGTH: 25
<212> TYPE: PRT
<213> ORGANISM: Homo sapiens

<400> SEQUENCE: 29

Leu Leu His Asp Lys Gly Lys Ser Ile Gln Asp Leu Arg Arg Arg Phe
1               5                   10                  15

Phe Leu His His Leu Ile Ala Glu Ile
            20              25
```